United States Patent [19]

Sinensky et al.

[11] Patent Number: 4,863,932

[45] Date of Patent: Sep. 5, 1989

[54] SQUALENE OXIDE CYCLASE INHIBITORS AND THERAPEUTIC USE THEREOF

[75] Inventors: Michael Sinensky, Denver, Colo.; Thomas A. Spencer, Hanover, N.H.

[73] Assignees: Somatogenetics International, Inc., Broomfield, Colo.; Dartmouth College, Hanover, N.H. ; a part interest

[21] Appl. No.: 167,124

[22] Filed: Mar. 11, 1988

[51] Int. Cl.[4] .................. A61K 31/47; A61K 31/045; C07D 217/04; C07C 35/27

[52] U.S. Cl. .................................... 514/307; 514/278; 514/729; 546/17; 546/18; 546/150; 568/817; 568/818

[58] Field of Search .......................... 546/150, 17, 18; 568/817, 818; 514/278, 307, 729

[56] References Cited

PUBLICATIONS

Gaspert, et al., "Chemical Abstracts", vol. 52, 1958, col. 11797g.
Sondheimer, et al., "J.A.C.S.", vol. 80, 1958, pp. 1967–1971.

Primary Examiner—Richard L. Raymond
Assistant Examiner—James H. Turnipseed
Attorney, Agent, or Firm—Iver P. Cooper

[57] ABSTRACT

Azadecalins and C-7 substituted decalins with squalene oxide cyclase inhibitory activity are useful as inhibitors of cholesterol synthesis and hence may be used in pharmaceuticals for regulating cholesterol levels in a mammal.

12 Claims, 9 Drawing Sheets

INHIBITION OF STEROL SYNTHESIS IN PRIMARY RAT HEPATOCYTES
BY THE SQUALENE OXIDE CYCLASE INHIBITOR LA-I-140

RESULTS ARE EXPRESSED AS THE RATIO OF INCORPORATION
OF ACETATE INTO DIGITONIDE PRECIPITABLE MATERIAL TO THAT
INCORPORATED INTO PHOSPHOLIPIDS

SQUALENE OXIDE CYCLASE INHIBITORS AND THERAPEUTIC USE THEREOF

BACKGROUND OF THE INVENTION

Cholesterol is the most abundant sterol in animal tissues. It is the precursor of a number of other steroids, including several steroid hormones.

Cholesterol is the product of a complex enzymatic proces. Beta-hydroxy-beta-methylglutaryl CoA is reduced by beta-hydroxy-beta-methylglutaryl CoA (HMG-CoA) reductase to yield mevalonic acid. Mevalonic acid is converted into squalene. Squalene is attacked by molecular oxygen, yielding squalene 2,3-epoxide, and this is cyclized into lanosterol by squalene oxide cyclase (SOC). Finally, lanosterol is converted into cholesterol. Several of the foregoing conversions are multi-step processes, and alternative pathways exist.

Nelson, et al., JACS 100: 4900 (1978) reported that 4, 4,10 beta-trimethyl-trans-decal-3beta-ol (TMD) specifically inhibited cholesterol biosynthesis in both rat liver enzyme preparations and in CHO cells. After incubation with rat liver homogenate, 4,4,10beta-trimethyl-trans-decalin-3beta, 7beta-diol was isolated as the major product of TMD metabolism. They postulated that TMD inhibited the cyclization of squalene oxide. A limited investigation into structure-activity relationships (by preparation and testing of the 4alpha,10 beta-dimethyl and 10 beta-methyl analogues) led to the conclusion that the 4alpha-methyl group played a significant role in the inhibition. (See also Chang, et al., J. Biol. Chem., 254: 11258, 1979). Nelson considered the hypothesis that 1-TMD acts as an analogue of a transition state between squalene oxide and the cyclized product, but noted that the inhibitory activity of d-TMD was inconsistent with that speculation. TMD and its 4,10 beta-dimethyl analogue are both reported to be nonoompetitive inhibitors of SOC, and they both had virtually no effect on the cyclases of higher plants. Duriatti, et al., Biochem. Pharmacol., 34: 2765 (1985).

Cattel, et al., Lipids, 21: 31-38 (1986) suggested broadly that inhibitors of 2,3-oxide squalene cyclases might behave as very selective hypocholesterolemic drugs. They focused on the use of 2-aza-2-dihydrosqualene and its derivatives. They did not express any interest in substituted or in trans-decalols.

SUMMARY OF INVENTION

It is undesirable to lower cholesterol levels by inhibiting the synthesis of the early precursors of cholesterol, since many other important biomolecules are prepared from the same compounds. For example, farnesyl pyrophosphate, a precursor of squalene 2,3-epoxide, is also converted to ubiquinone (coenzyme Q), or to dolichol (necessary for glycosylation of proteins). Mevalonic acid plays an essential role in DNA replication. Mevinolin, an anti-cholesterolemic drug which inhibits HMG-CoA reductase, results in defects in the glycosylation of proteins in lymphocytes which can persist for ten months after administration.

We have found that certain decalins and azadecalins show strong squalene oxide cyclase inhibitory activity in rat liver hepatocytes. They are expected to be of value as cholesterol lowering agents.

The squalene oxide cyclase inhibitors of this invention may have the following structure:

Formula (I)

wherein $R_1$ is methyl, etyyl, or forms a cyclopropane ring with $R_2$;

$R_2$ is methyl, ethyl, or forms a cyclopropane ring with $R_1$, but $R_1$ and $R_2$ are not both ethyl;

$R_3$ is hydrogen, an alkyl of no more than 5 carbon atoms, fluorine, chlorine or bromine;

$R_4$ is hydrogen, an alkyl of no more than 5 carbon atoms, fluorine, chorine or bromine, where $R_3$ and $R_4$ may be the same or different, and where $R_3$ and $R_4$ may form a cyclopropane (CyPrp) ring;

$R_5$ is hydrogen, methyl, ethyl, propyl, isopropyl, butyl or hydroxymethyl and $R_6$ is hydrogen, methyl or ethyl; but excludino TMD oer se, for which $R_1$ is methyl, $R_2$ is methyl and $R_6$ is methyl, and $R_3$, $R_4$ and $R_5$ are all hydrogen.

While TMD is an effective inhibitor of squalene oxide cyclase in in vitro microsomal assays, we have found that in cultures of rat hepatocytes (a system that contains all of the metabolic machinery of drug detoxification), and in in vivo experiments, TMD is actually an unexpectedly poor inhibitor of SOC.

We attribute this unexpectedly poor performance to metabolism of TMD at the C-7 position by 7-alpha-hydroxylase. Thus, we propose to modify TMD by a protective substitution at C-7.

Thus in a preferred embodiment, there is a substituent other than hydrogen at $C_7$ or $C_9$, especially both, i.e., $R_3$, $R_4$, and $R_5$ are not hydrogen.

In especially preferred embodiments, $R_1$ through $R_6$ have the following assignments:

|  | $R_1$ | $R_2$ | $R_3$ | $R_4$ | $R_5$ | $R_6$ |
| --- | --- | --- | --- | --- | --- | --- |
| LN I-83 | Me | Me | F | F | H | Me |
| PCR II-8B | Me | Me | CyPrp | CyPrp | H | Me |
| PCR II-23 | Me | Me | Me | Me | H | Me |
| JW I-60 | Me | Me | H | H | $CH_2OH$ | Me |

Compounds PCR II-8B and II-23 are especially preferred.

Our SOC inhibitors also include a related family of compounds having a heterocyclic nitrogen as shown in the formula below, with $R_1$–$R_7$ as stated above, and where $R_7$ is hydrogen, methyl or ethyl:

Formula (II)

Preferably, the molecule is isolated as a salt of hydrochloric, sulfuric, phosphoric or an organic acid.

The substitutions at C-4 (RI and R2), C-9 (R5) and C-10 (R6) increase the resemblance of the illustrated inhibitor to the enzymatic product lanosterol (see FIG. 8). It is also possible to consider LA I-140 an analogue of transition state 2 and JW I-60 an analogue of the bicyclic 4 (both in FIG. 8), however, the resemblances are crude.

BRIEF DESCRIPTION OF THE DRAWINGS

FIG. 2 Views (a), (b) and (c) illustrate the inhibatory effect of (a) LA-I-140 (b) PCR II-23 and (c) PCR II-8B on sterol synthesis in primary rat hepatocytes. The abbreviation "st/ppl" signifies "sterol-to-polar lipid" ratio.

DETAILED DESCRIPTION OF THE INVENTION

Example 1 (LA I-140 Synthesis)

Synthesis of 4,4,10-trimethyl-trans-3-azadecalin (LA-I-140) began with oxidation of TMD (5, FIG. 1) to obtain the known ketone 6. (Czarny, M.R., Ph.D. Dissertation, Dartmouth College, 1976; Gaspert, et al., J. Chem. Soc., 1958, 624-628.

This ketone was converted to lactone 7 by a Baeyer-Villiger oxidation. Meinwald, et al., J. Org. Chem., 29:2914-19 (1964). Pyrolysis of 7 cleanly afforded unsaturated acid 8. A modified Curtius reaction (for which see Shiori, et al., J. Am. Chem. Soc., 94: 6203-5 (1972); Capson and Poulter, Tetrahedron Lett., 19B4. 3515-18) then produced carbamate 9.

In a key step, amidomercuration of 9 yielded bicylic carbonate which was subjected to acidic hydrolysis to provide the desired hydrochloride 2. The synthesis is described in further detail below.

4,4,10,beta-Trimethyl-trans-decal-3-one (6). Oxidation of 2.35 g (11.9 mmol) of TMD (5), which had been prepared as previously described[3,9], with Jones reagent[10] at 0° for 20 minutes afforded, after a normal workup, 2.10 g (90%) of 6, bp 90°-93° Torr), which had spectroscopic properties consistent with those published for 6[3].

2,2,7-Trimethyl-trans-3-oxa-4-oxobicyclo [5.4.01 undecane (7). According to a procedure of Meinwald and coworkers[4], a solution of 6.20g (31.9 mmol) of 6 in 20 mL of $CH_2Cl_2$ was added dropwise to a solution of 9.60g (44.5 mmol) of m-chloroperoxy-benzoic acid (Aldrich, 80-85%) in 75 mL of $CH_2Cl_2$. The mixture was protected from light with Al foil and stirred at room temperature for 36 hours, at which time TLC showed no 6 remaining. The precipitate was removed by filtration, and the filtrate was washed successively with 30 mL of 10% aqueous $Na_2SO_3$ solution, 2×30 mL of saturated aqueous $NaHCO_3$ solution, 10 mL of water, and 20 mL of brine, dried over $MgSO_4$, and evaporated to afford 7.41 g of material which partially solidified on standing in the refrigerator. Trituration with 10 mL of hexane furnished 4.30 g of 7, mp 55°-58° C. The residue was flash chromatographed with 5:1 hexane:ethyl acetate to afford an additional 1.84 g of 7, mp 54°-57° C., for a total yield of 6.14 g (92%) of 7,which was homogeneous by TLC. Two recrystallizations form hexane afforded an analytical sample of 7: mp 58.5°-59.5° C; IR 1730 $cm^{-1}$; $^1H$ NMR delta 2.70 (m, 2) 2.0–1.0 (m, 20 with singlets at 1.40 and 1.10); $^{13}C$ NMR delta 175.60, 86.80, 54.56, 45.15, 38.55, 36.90, 33.35, 32.18, 26.91, 25.25, 23.84, 21.49, 18.73; MS m/e 210. Anal. Calcd. for $C_{13}H_{22}O_{22}$; C, 74.23; H, 10.54. Fund: C, 74.51; H, 10.65.

1 alpha- [2-Carboxymethyl1-1beta-methyl-2beta-isopropenylcyclohexane (8). A 5-ml addition funnel situated on the top of a pyrolysis tube which had been heated to 420° C was charged with 3.90 g (18.5 mmol) of 7. After the 7 had melted, it was slowly dropped through the hot column accompanied by a stream of $N_2$. Material emerging from the column was collected in a trap at dry ice temperature. After the addition of 7 was completed, the column was flushed with 10 mL of hexane. Evaporation yielded 3.70g (95%) of 8, mp 59°-63° C., which was homogeneous by TLC. Two recrystallizations from ether:hexane afforded an analytical sample of 8: mp 68°-70° C; IR 3250-2550, 1715, 1645, 900 $cm^1$; $^1H$ NMR delta 10.10 (brs, 1), 4.82 (m,2), 2.35(m, 2), 2.10–1.0(brm 17, With sharp singlets at 1.75 and 0.89); $^{13}C$ NMR delta 181.48, 147.48, 112.90, 53.17, 38.28, 37.74, 35.85, 28.72, 28.15, 26.74, 23.43, 21.93, 18.79; MS, m/e 210. Anal. Calcd, for C13H2202 C, 74.23, H, 10.54. Found: C, 74.46; H, 10.64.

N-Carbobenzyloxy-1alpha-[2-aminoethyl1-1beta-methyl-2 beta-isopropenylcyclohexane (9). To a solution of 0.720 g (3.42 mmol) of 8 in 3 mL of toluene which had been freshly distilled from sodium, was added 0.47 mL of freshly distilled triethylamine and 0.940 g of (3.42 mmol) of diphenylphosphorylazide (Aldrich). The resulting mixture was heated at 85°-90° C. for 1 hour, and then 0.940 g (8.60 mmol) of benzyl alcohol was added and the yellowish mixture was heated at 85-°90° C. for an additional 4 hours. The mixture was evaporated and the residue wa5 dissolved in 30 mL of $CH_2Cl_2$, which was then washed with 10 mL of 5% aqueous NaOH solution, 10 mL of water, and 10 mL of brine, dried over $MgSO_4$, and eaporated to afford 1.52g of viscous yellow oil. Flash chromatography with 500 mL of 10:1 hexane:ethyl acetate and then 1000 mL of 4:1 hexane:ethyl acetate yielded 0.52 g (78%) of 9 as a clear liquid which solidified on standing and which was homogenous by TLC. Recrystallization from hexane gave an analytical sample of 9: mp 68°-69.5° C; IR 3340, 1710, 1650 $cm^{-1}$; $^1H$ NMR delta 7.36(s, 5), 5.13 (s, 2), 4.76(m, 3), 3.20 (m, 2), 1.76 (s, 3), 1.50 (bm, 11), 0.89 (s, 3); $^{13}C$ NMR delta 147.60, 136.61, 128.40, 128.10, 127.99, 127.95, 112.81, 66.44, 53.51, 43.23, 38.47, 36.63, 35.76, 27.90, 26.70, 23.29, 21.87, 18.97; MS, m/e 315. Anal. Calcd. for $C_{20}H_{29}NO_2$: C, 76.15; H, 9.26; N, 4.43. Found: C, 76.19; H, 9.30; N, 4.36.

4,4,10-Trimethyl- 3-carbobenzyloxy-trans-3-azadecalin(10). A mixture of 1.02 g (3.17 mmol) of 9 and 1.60 g (3.80 mmol) of mercuric trifluoroacetate (Aldrich) in 45 mL of nitromethane, which had been freshly distilled from calcium hydride, was stirred at room temperature under nitrogen and covered with Al foil. TLC after 1 hour showed the presence of some 9, so 0.800g (1.80 mmol) of additional mercuric trifluoroacetate was added and the mixture was stirred for another 0.5 hour. The reaction mixture was evaporated, and the residue was taken up in 10 mL of CH2Cl2, which was then filtered. The filtrate was added slowly to a vigorously stirred solution of 3.50 g of benzyltriethylammonium chloride (Aldrich) in 20 mL of 10% aqueous NaOH solution. To this mixture was then slowly added a solution of 0.115 g (3.02 mmol) of NaBH4 in 6 Ml of 10% aqueous NaOH solution, during which time the mixture turned black. After the black, metallic particles settled on the bottom of the flask (about 15 minutes), the supernatant was carefully decanted and the residue was rinsed with ca. 10 mL of $CH_2Cl_2$. These layers were separated and the aqueous layer was extracted with 3×15 mL of $CH_2Cl_2$. The combined organic layers were washed with 2×15 mL of brine, dried over MgSO4, and evaporated to give 1.74g of yellow oil, which was flash chromatographed with 10:1 hexane:ethyl acetate to afford 0.420g (41%) of 10, which solidified on standing and which was homogeneous by TLC. Recrystallization from hexane gave an analytical sample of 10: mp 47.5°-49° C., IR 1710 cm$^{-1}$; $^1$H NMR delta 7.38 (m, 5), 5.13 (s, 2), 3.76(m, 1), 3.43 (m, 1), 2.0–1.0(m, 17, with sharp singlets at 1.55, 1.30 and 1.06); $^{13}$C NMR delta 157.30, 137.14, 128.36, 127.74, 127.68, 66.44, 58.63, 53.03, 44.45, 40.04, 39.05, 32.23, 28.76, 27.59, 23.66, 21.81, 20.03, 19.12, MS m/e 315. Anal. Calcd. for $C_{20}H_{29}NO_2$: C, 76.15; H, 9.26; N, 4.43. Found: C, 75.99; H, 9.24, N. 4.30.

Also obtained from the flash chromatography was 0.220 g (21%) of unreacted 9.

4,4,10-Trimethyl-trans-3-azadecalin Hydrochloride) (LA I-140) (2). A solution of 0.400 g (1.26 mmol) of 10 in 9 mL of glacial acetic acid which had been saturated with HCl gas was stirred at room temperature for 1 hour and at 55-60° C for 6 hours, with a slow stream of HCl gas bubbling through the mixture. The mixture was concentrated in vacuo to one-third its original volume and diluted with 80mL ether, causing formation of a white precipitate. After the mixture had been stored in the freezer overnight, filtration yielded 0.220 g (80%) of 2, mp 218°-220° C. (dec.). Three recrystallizations from absolute ethanol:ether gave an analytical sample of 2: mp 226°-227° C. (dec.); IR 2480-2440 cm$^{-1}$; $^1$H NMR delta 9.40 (brs, 2), 3.11 (m, 2), 1.8-0.95(brm, 20, with sharp singlets at 1.47, 1.26, and 0.97); 13C NMR delta 58.10, 50.60, 43.63, 36.73, 36.40, 32.15, 28.63, 26.43, 21.52, 20.98, 18.77, 18.60. Anal. Calcd. for $C_{12}H_{24}ClN$: C, 66.18; H, 11.10; Cl 16.32; N, 6.43. Found: C, 66.06; H, 11.12; Cl, 16.26; N, 6.42.

The ability of 2 to inhibit sterol synthesis was assayed by the following procedure.

Primary rat hepatocytes (2.2×10$^6$ cells/60 mm plate) were incubated overnight with various concentrations of inhibitor. The cells are then pulsed for 1 hour with tritiated acetate, harvested by centrifugation and the lipids extracted (Bligh, E. G. and Dyer, W. J. *Can. J. Biochem. Physiol.* 1959, 37. 911-917). Polar lipid are separated from neutral lipids by silicic acid chromatography. The polar lipids are collected and counted for radioactive acetate incorporation, and used as control for total acetate metabolism. The neutral lipid fraction is saponified and sterols precipitated with digitonide. The digitonide precipitate is counted to measure total incorporation of radioactive acetate into sterols.

Figure 1:
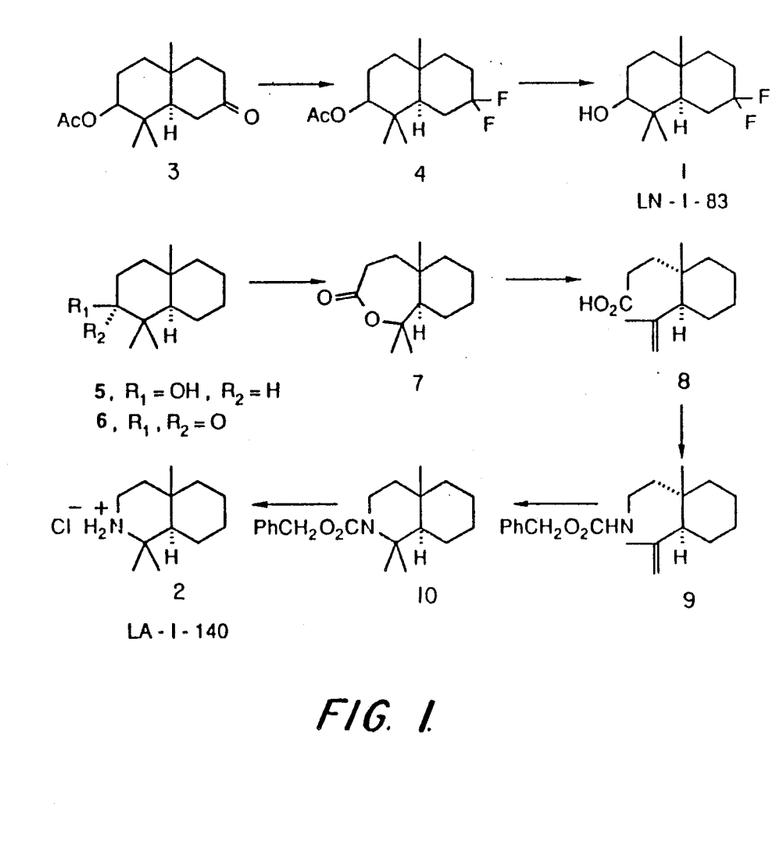
FIG. 1 shows the scheme for the synthesis of LN-I-83 1 and LA-I-140 2.

The results are shown in FIG. 1. As illustrated, 40 ug/ml reduces sterol synthesis in primary rat hepatocytes to one-half of their normal levels.

The cytotoxicity of LA-I-140 was also investigated. Cytotoxicity was measured by inoculating 500 fibroblast cells in a 35 mm dish in F12 media containing 5% fetal calf serum with various concentration of inhibitor. The cells were then incubated until colonies were formed. The cytotoxicity, or relative plating efficiency, was determined as a ratio of the number of surviving colonies in treated cultures with the number of colonies in untreated cultures. As may be gleaned from FIG. 3, LA-I-140 is essentially non-cytotoxic over a concentration range of up to 40 ug/ml.

Example 2 (LN I-83 Synthesis)

The synthesis of LN-I-83 1 (see FIG. 1) commenced from the known acetox Nelson, et al., Bioorganic Chem., 11: 371-81 (1982); Mukherjer and Dutta, J. Chem. Soc., 1960, 67-71. Fluorination was achieved by use of diethylaminosulfur trifluoride (DAST), see Middleton, J. Org. Chem., 40:574-78 (1975), leading to acetoxydifluoro compound 4. Hydrolysis of the protecting group then yielded the 7,7-difluoro-TMD 1.

4,4,10, beta-Trimethyl-7,7-difluoro-3beta-acetoxy-transdecalin (4). According to the procedure of Ohtsuka, et al., Chem. Pharm. Bull., 34: 2780-85 (1986), a solution of 0.51g (2.01 mmol) of 3, prepared as previously described, in 3 mL of CH2Cl2 was added to a solution of 0.65g (4.02 mmol) of diethylaminosulfur trifluroide (DAST) (Aldrich) in 2 mL of CH2Cl2 at 0° C. The solution was stirred at room temperature for 48 hours, after which time the reaction was quenched with 5% Na2CO3 solution. The aqueous layer was extracted with ether, and the organic layer was dried over MgSO4. The solvent was evaporated to yield 0.50g of yellow oil. Flash chromatography with 3:17 ethyl acetate:hexane and then 3:7 ethyl acetate:hexane gave two compounds; the first was 0.38g (69%) of 4 as a yellow oil which crystallized upon standing, and the second was 44 mg of impure 3 as a brown oil. Five recrystallizations of 4 from ether:hexane gave an analytical sample: mp 71°-72° C; IR 1745 cm.$^{-1}$; $^1$H NMR delta 4.49 (dd, J=10.5 Hz, J=5.4 hz, 1), 2.04 (s, 3), 1.2–2.0 (m, 11), 0.98 (s, 3), 0.85 (s, 3), 0.84 (s, 3). Anal. Calcd. for $C_{15}H_{24}O_2F_2$: C, 65.67; H, 8.82. Found: C, 65.68; H, 8.87.

4,4,10 beta-Trimethyl-7,7-difluoro-trans-decal-3beta-ol (LN I-83) (1). To a solution of two pellets of KOH in 1 mL of water and 5mL of methanol at room temperature was added 0.26g (0.94 mmol) of 4. The resulting mixture was stirred overnight. The solvent was evaporated, and the resulting residue was partiioned between water and ether, the aqueous layer was acidified with 10% HCl solution and extracted with ether. The combined organic layers were dried over MgSO4, and the solvent was evaporated to afford a yelow oil, which crystallized upon addition of a small amount of hexane to yield 0.22 g (100%) of 1. Four recrystallizations of 1 from ether:hexane gave an analytical sample: mp 93°-94° C; IR 3350 cm$^{-1}$; $^1$H NMR delta 3.27 (m,l), 1.15-2.08 (m, 11), 0.99 (s, 30, 0.97(s, 3), 0.79 (s, 3); $^{13}$C NMR delta 124.5 (dd, $J_{CF}$=243 Hz, $J_{CF}$=239 Hz), 48.00 (d, $J_{CCCF}$=8.9 Hz), 40.29 (d, $J_{CCCF}$=10.2 Hz), 38.62, 38.59, 38.51, 38.27, 33.27, 30.75 (dd, $J_{CCF}$=25.5, $J_{CCF}$=22.0 Hz), 29.96 (dd, $J_{CCF}$=25.9 Hz, $J_{CCF}$=22.4 Hz), 27.29, 18.17, 14.81. Anal. Calcd. for $C_{13}H_{22}OF_2$: C, 67.21; H, 9.55. Found: C, 67.30; H, 9.62.

Example 3 (PCR II-8B Synthesis)

Figure 3:
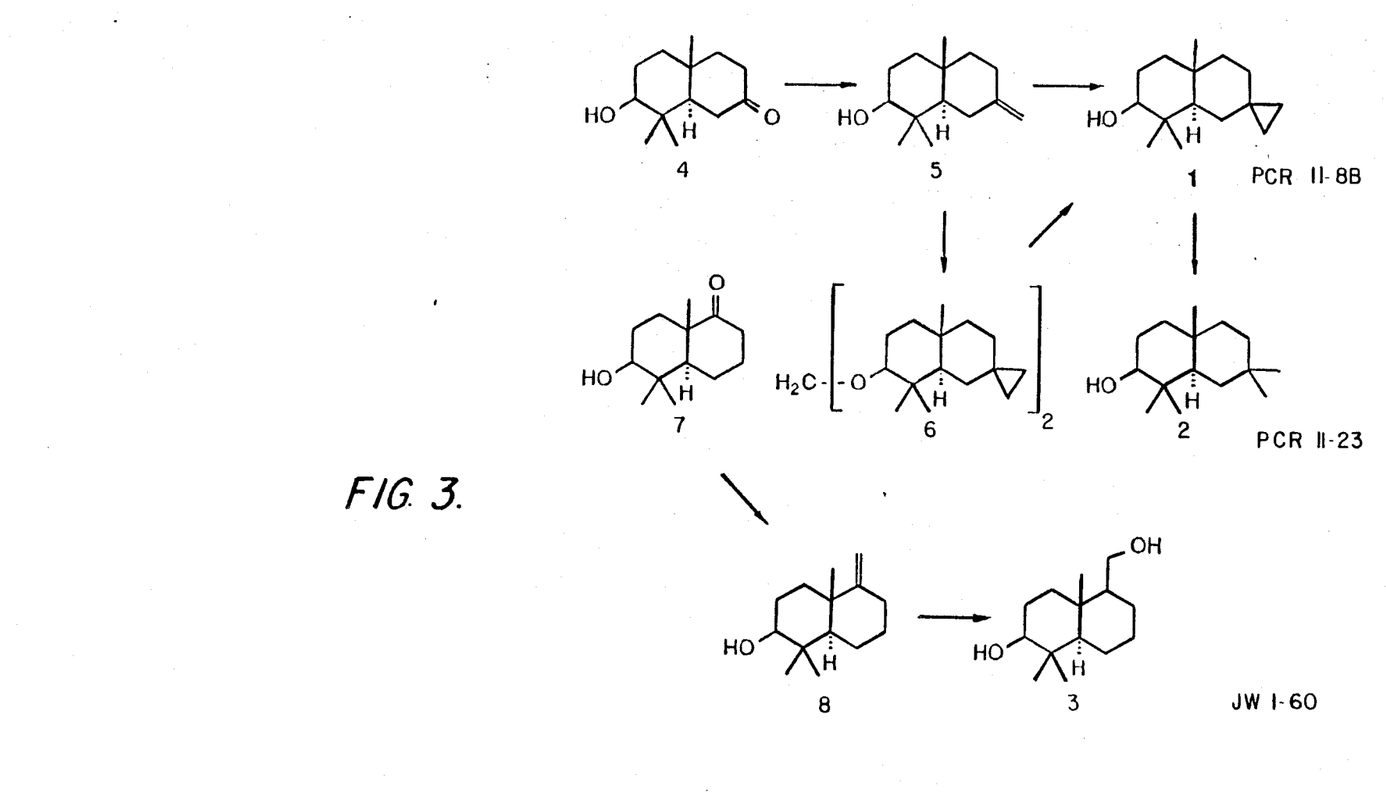
FIG. 3 shows the scheme for the syntheses of PCR 11-8B 1, PCR II-23 2 and JW I-60 3.
Figure 4:
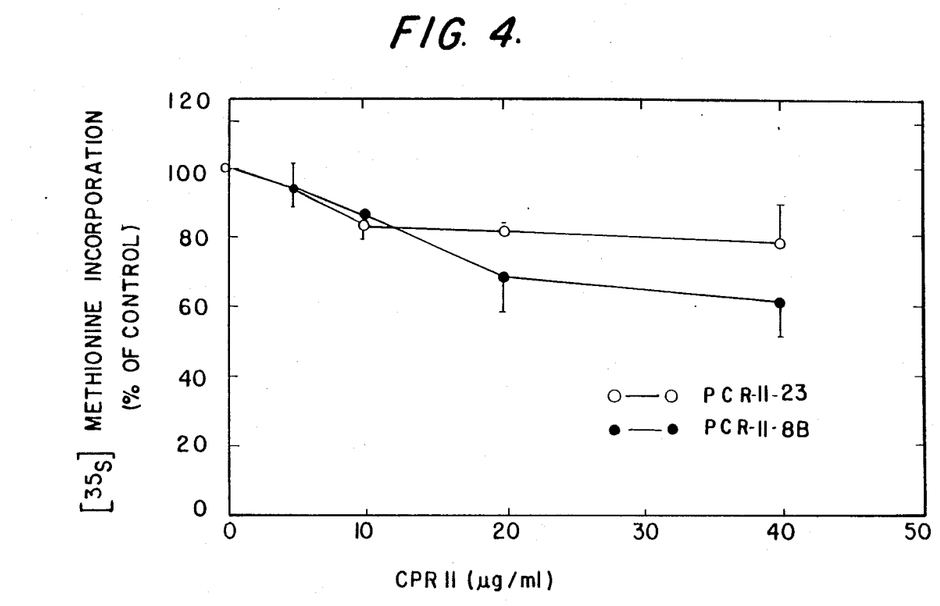
FIG. 4 illustrates the effects of PCR.II-8B and II-23 on hepatic protein synthesis.
Figure 5:
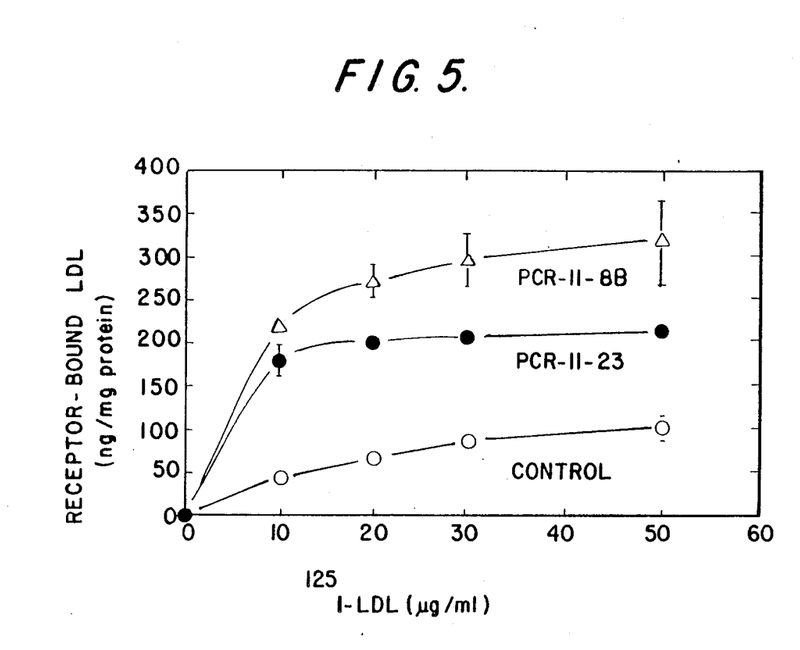
FIG. 5 shows the effect of PCR-II.8B and PCR-II-23 on the LDL receptor of HepG2 cells.
Figure 6:
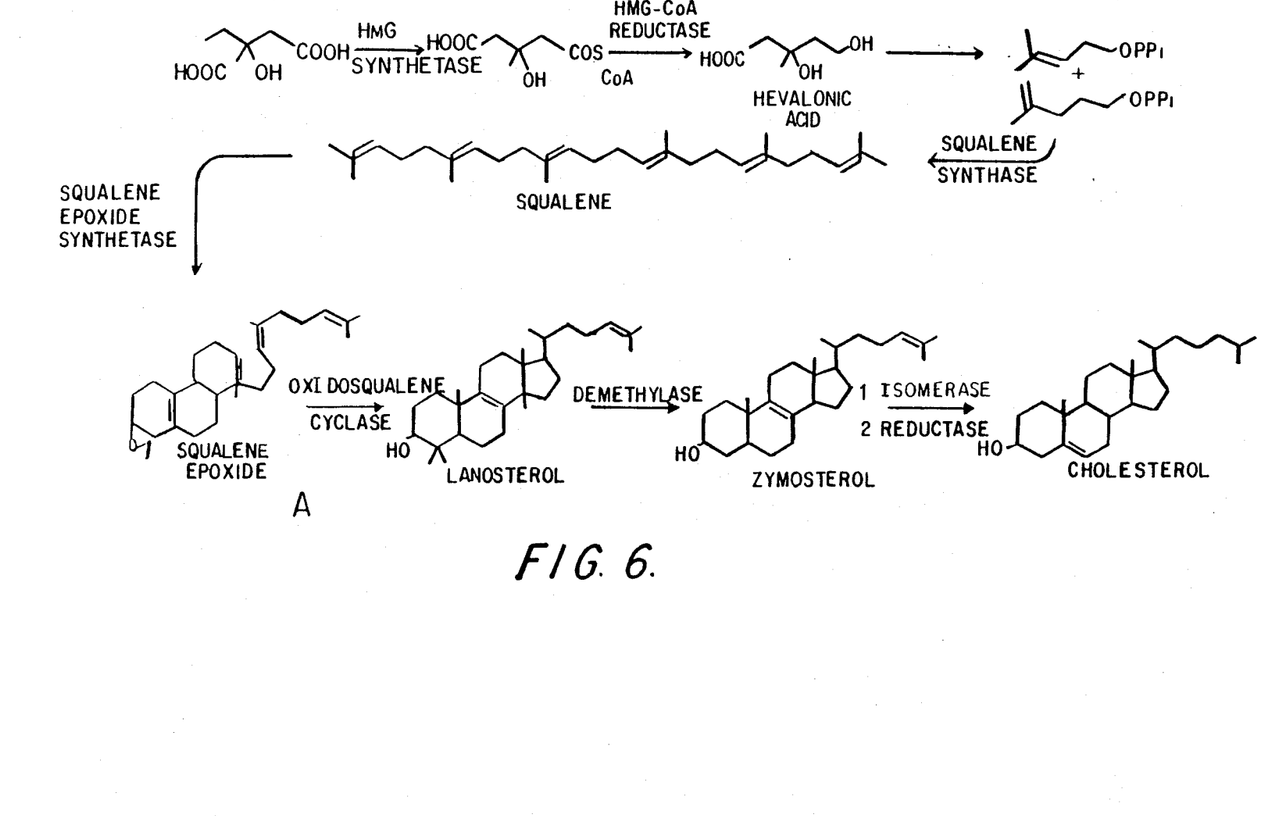
FIG. 6 outlines the biosynthesis of cholesterol.
Figure 7:
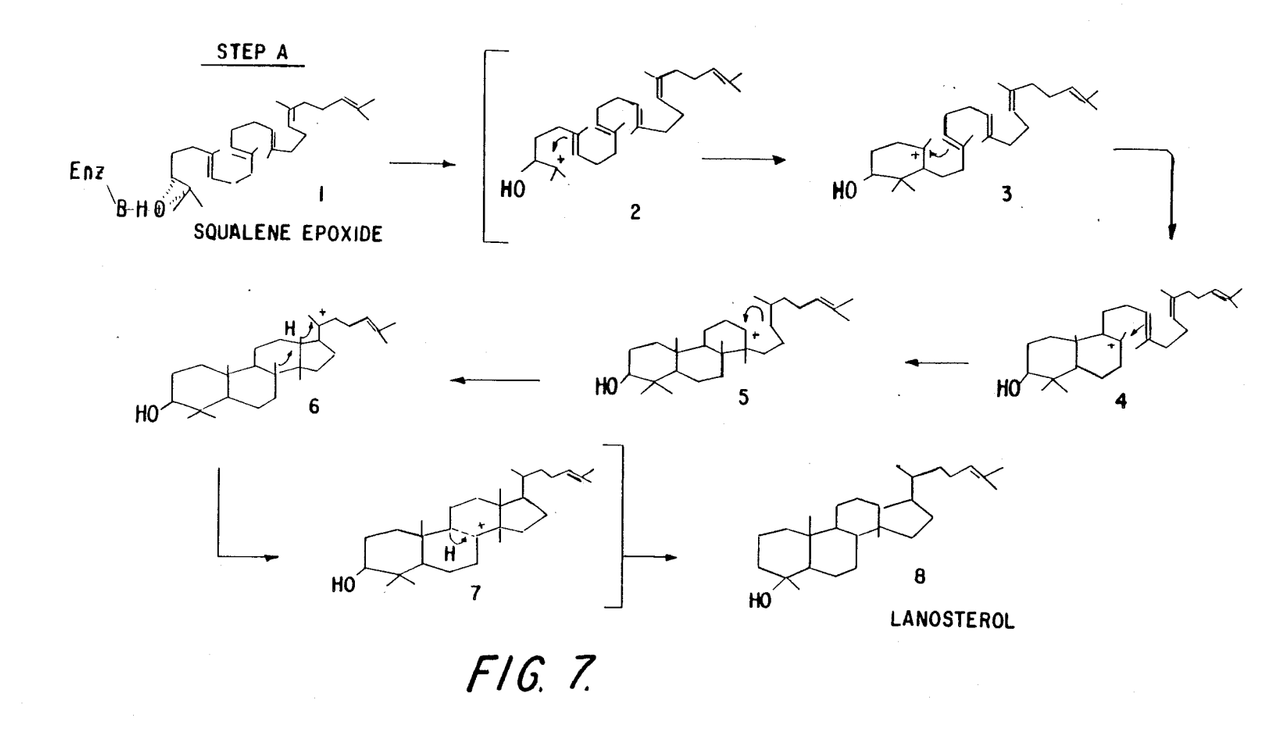
FIG. 7 diagrams a postulated mechanism for the cyclization of squalene epoxide into lanosterol.

(4,4,10beta-trimethyl-trans-decal-3 beta-ol)--7-spiro-1'-cyclopropane (PCR II-8B) was prepared from a ketoalcohol by a two-step process (FIG. 3). The ketoalcohol is known. See Nelson, et al., Bioorganic Chem., 11: 371-81919820; Levisalles, et al., Bull. Soc. Chem. Fr., 299-302 (1968); Levisalles, et al., Id., 4314-18 (1972); Mori, et al., Tetrahedron, 42: 291-4 (1986). The ketoalcohol is converted into a methylidene alcohol by a Witting reaction. Conia, et al., Bull. Soc. Chim. Fr., 1936-38 (1967). The latter is converted into PCR II8-B by a modified Simmon-Smith reaction. See Denis, et al., Synthesis, 549-51 (1972); Miyano, et al., J. Chem. Soc. Chem. Commun., 1418-19 (1971); Furukawa, et al., Tetrahedron, 24: 53-58 (1968). The small amount of formaldehyde acetal byproduct may be hydrolyzed to obtain PCR II 8-B.

The synthesis is described in greater detail below.

4,4,10beta-Trimethyl-7-methylidene-trans-decal-3beta-01(5). To a suspension of 0.74g (6.8 mmol) of sodium in 10 mL of benzene under N2 at room temperature was added 2.41g (6.75 mmol) of methyltriphenylphosphonium bromide. The mixture was stirred for 15 mins., then cooled to 0° C. (icewater bath), and a solution of 0.56g (2.7 mmol) of 4,4,10-beta-trimethyl-7-beta-trans-3-beta-decalol 4, prepared as previously described in 10 mL of benzene was added rapidly. After 4 mins., the cooling bath was removed and the reaction mixture was stirred for 1 hr. at room temperature. It was then diluted with 20 mL of benzene and filtered through a two inch thick pad of florisil, under suction, and the pad was washed with 3×10 mL of benzene. The filtrates were combined and evaporated to yield 0.48g of product which was flash chromatographed to afford 0.44g (78%) of 5, mp 80°-81 ° C. after recrystallization from hexane: IR 420, 2920, 1650 cm$^{-1}$; $^1$H NMR delta 4.61 (s, 2H), 3.22 (dd, J=6.6, 7.2 Hz, 1H), 2.50-1.30 (m, 12H), 0.99 (s, 6H), 0.79 (s, 3H); $^{13}$C NMR delta 149.95, 106.92, 79.04, 53.25, 45.47, 39.49, 38.84, 33.80, 30.98, 30.54, 27.50, 18.71, 14.79; MS, m/e 208 (M+, 25.6), 193 (45.34), 180 (20.66), 175 (39.34), 149 (29.66), 147 (25.60), 139 (53.97), 137 (22.04), 135 (24.35), 121 (45.60), 119 (25.17), 111 (51.38), 109 (51.38), 107 (49.05), 105 (24.65), 96 (25.22), 95 (100). Anal, calcd for C14H240: C, 80.71; H, 11.61. Found: C, 80.83; H, 11.58.

(4,4,10beta-Trimethyl-trans-decal-3beta-ol)-7-soiro-1'-cyclopropane (PCR II-8B) (1)

Procedure A: To a stirred solution of 14 mg of silver acetate in 15 mL of acetic acid at 80° C. under argon was added, all at once, 2.31g (0.035 mmol) of granular zinc. The mixture was stirred for 30 seconds and the acetic acid was removed via syringe. A fresh 15 mL of acetic acid was added and stirred for 3 minutes before being withdrawn. Anhydrous ether (20 ml) was introduced via syringe, the mixture was stirred for 5 minutes, and the ether was removed. This process of washing with 20 mL of ether was repeated 4 times. Anhydrous ether (20 mL) was again added followed by 100 mg of silver wool. To this stirred mixture was added a solution 0.37g (1.8 mmol) of 5 in 10 mL of ether as rapidly as possible. Freshly distilled diiodomethane (4.74g, 17.7 mmol) was added dropwise and the reaction mixture was heated at reflux for 12 hours. It was then cooled to 0° C (ice-water bath), diluted with 20 mL of ether and 1 mL of pyridine was added dropwise with vigorous stirring. After being stirred for 30 minutes, the resulting suspension was filtered under suction. The precipitate was washed with 3×10 mL of ether and the filtrate and washings were combined. To this solution was added a drop of pyridine to determine whether the precipitation was complete. As no precipitate was observed, the solvents were evaporated to afford 0.51g of crude product which was flash chromatographed to yield 0.14g (35%) of 1, mp 88°-90° C. after recrystallization from hexane; IR; 3340, 3080, 2950 cm$^{-1}$; $^1$H NMR delta 3.24 (dd, J=6.9, 9 Hz, 1H), 2.0-0.50 (m, 12H), 0.95 (s, 3H), 0.90 (s, 3H), 0.74 (s, 3H), 0.29 (m, 4H); 13C NMR delta 79.19, 51.44, 43.88, 39.90, 38.34, 33.65, 31.40, 30.99, 27.61, 19.40, 18.76, 15.07, 13.40, 11.75; MS m/e, 222 (M+, 6.7), 204 (24.53), 189 (48.91), 175 (25.58), 165 (21.92), 161 (25.00), 137 (21.92), 136 (22.14), 135 (38.49), 133 (24.13), 123 (24.13), 122 (35.71), 121 (34.73), 119 (21.27), 111 (24.31), 109 (100) Anal. Calcd for C15H260; C, 81.02; H, 11.79. Found: C, 80.94; H, 11.77.

Also eluted Were: 0.22g (27%) of 6, mp 136°-140° C.; IR 3060 , 2920 cm$^{-1}$; $^1$H NMR delta 4.81 (s, 2H), 3.1 (dd, J=4.39, 4.34 Hz, 2H), 2.0-0.50 (m, 22H), 0.96 (s, 6H), 0.87 (s, 6H), 0.75 (s, 6H), 0.28 (m, 8H); $^{13}$C NMR delta 94.82, 85.72, 51.92, 43.92, 39.92, 38.27, 33.53, 31.42, 31.11, 27.93, 24.53, 19.44, 18.82, 16.07, 13.46, 11.77; MS m/e 426 (M-CH2O 0.2), 206 (16.02) 205 (100.00), 204 (78.54), 149 (79.95), 135 (34.24), 123 (22.13), 121 (29.64), 109 (59.20), 107 (28.22); and 0.02g (5%) of 5.

Procedure B: To a solution of 0.21g (1.0 mmol) of 5 in 4 mL of benzene under argon at room temperature was added 1.82 mL of a 1.1 M of diethylzinc in toluene. To this colorless solution was added 0.24 mL (3 mmol) of freshly distilled diiodomethane and the resulting mixture was stirred for 30 minutes during which time a cloudy white precipitate formed. The argon was replaced by dry oxygen, which was swept over the reaction mixture as the precipitate turned light pink. The temperature was raised by use of a sand bath at 68° C. and stirring was continued for 2 hours. The mixture was then cooled to room temperature and was poured slowly into 1 mL of 1% aqueous HCl. The mixture was extracted with 3×15 mL of ether, washed with saturated aqueous sodium bicarbonate, water, and saturated aqueous sodium chloride. The extracts were dried over anhydrous sodium sulfate and evaporated to afford 0.57g of residue which was flash chromatrographed to yield 0.13g (59%) of I and 0.03g (7%) of 6.

Figure 2A:
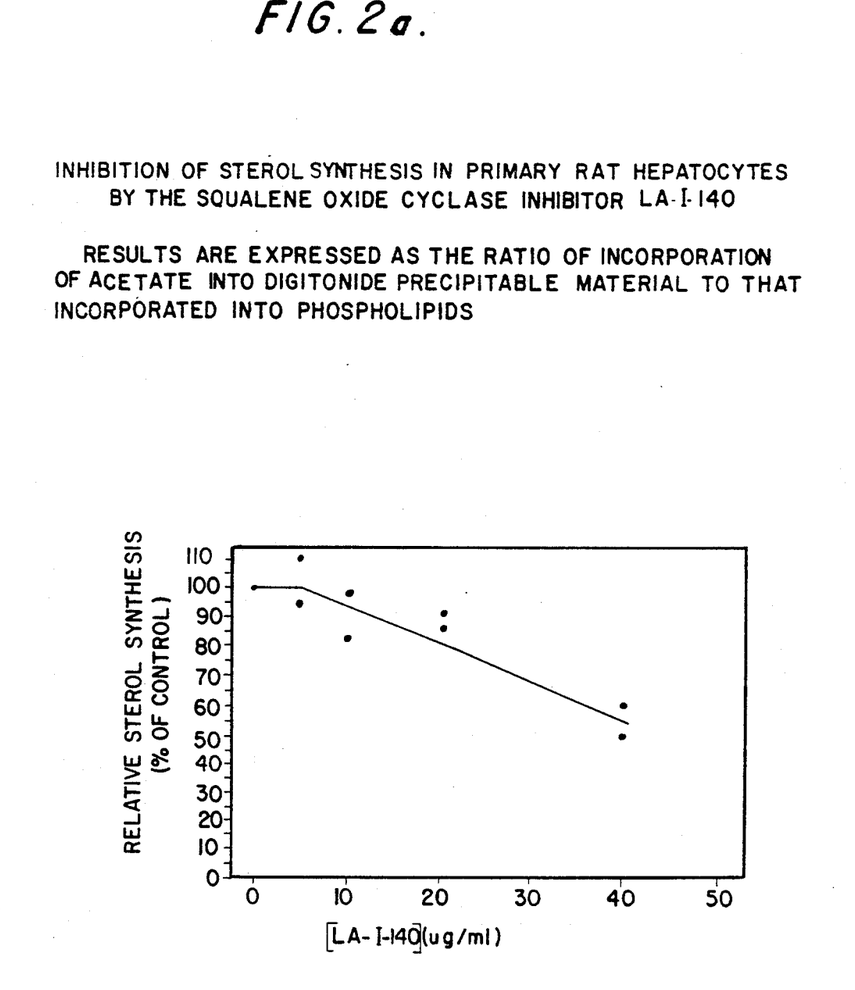
Figure 2B:
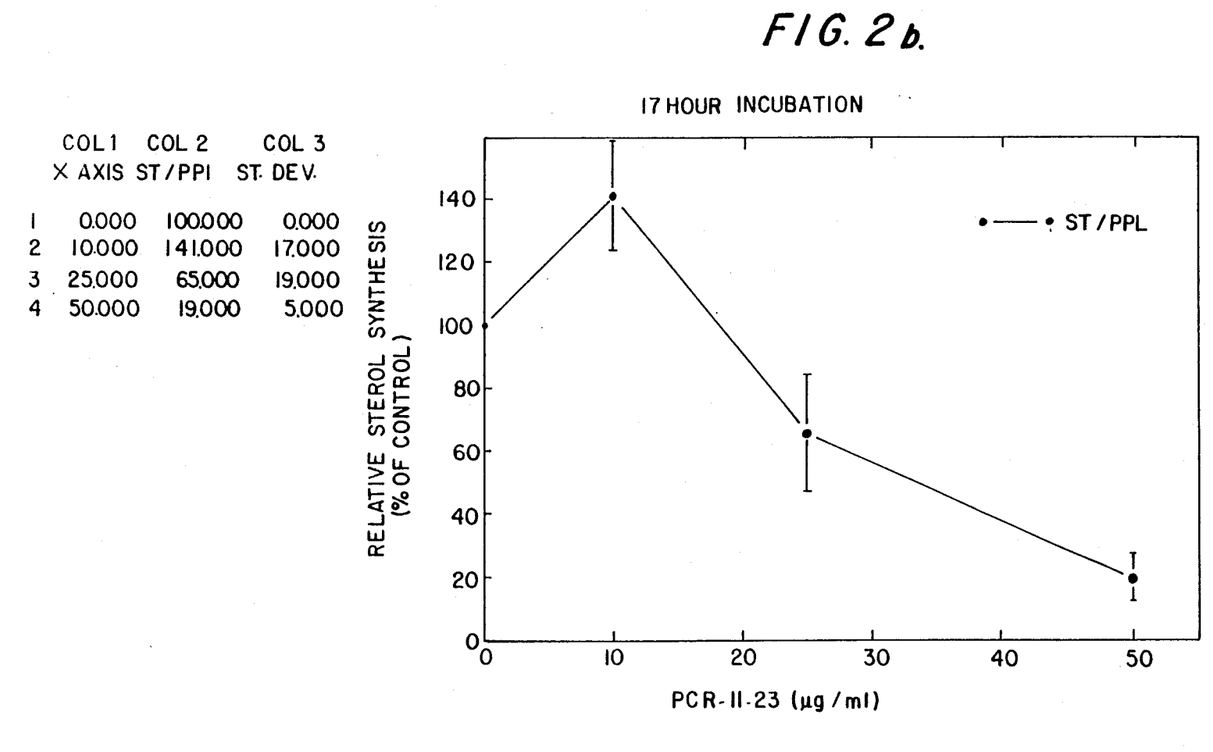
Figure 2C:
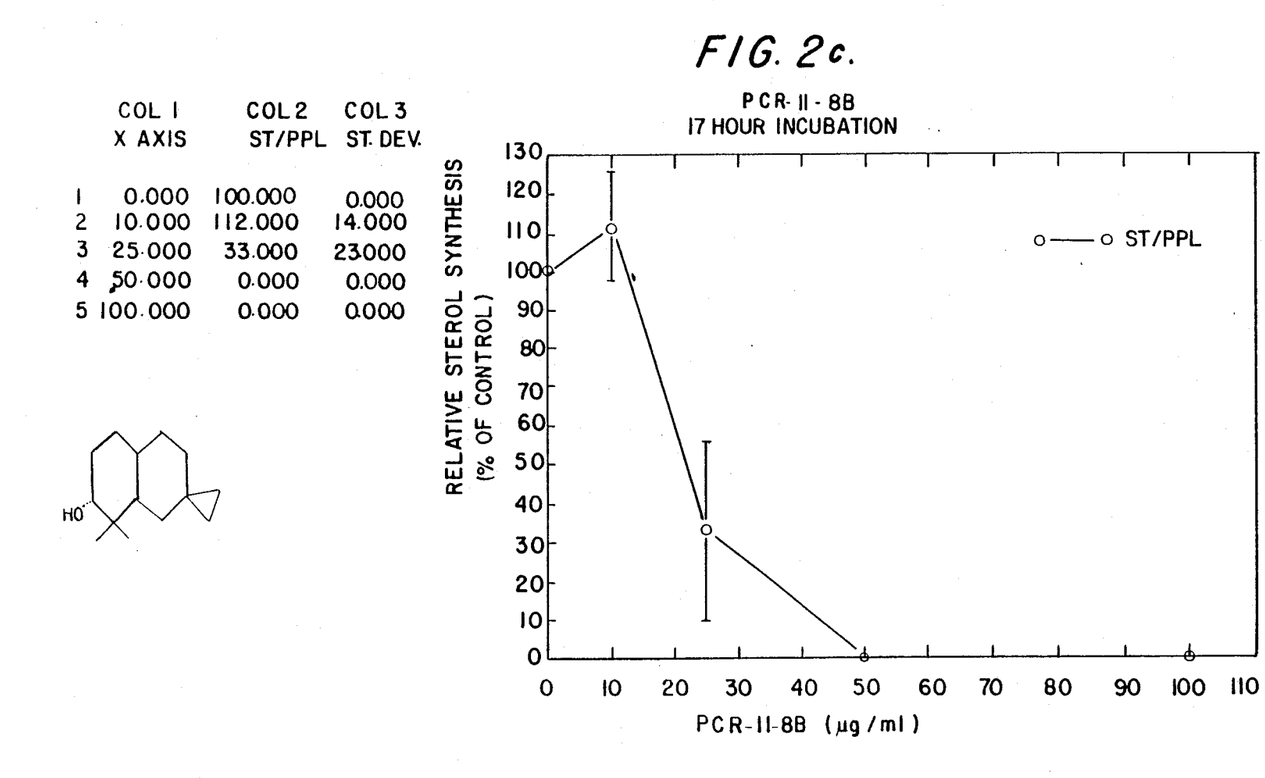

At 50 ug/ml of PCR II-8B there was no detectable sterol biosynthesis by primary rat hepatocytes of our assay. See FIG. 2(C).

Example 4 (PCR II-23 Synthesis)

4,4,7,7, 10-pentamethyl-trans-decal-3 beta-ol (PCR II-23) has also been studied. It was obtained by hydrogenolysis of PCR II-8B.

See Newham, Chem. Rev., 63: 123-37 (1963); Opolzer, et al., Helv. Chim. Aota, 67: 1157-67 (1984): Trost, J. Am. Chem. Soc., 104: 886-87 (1982); Strekowski, et al., J. Org. Chem., 51: 4836-39 (1986).

The synthesis is more fully set forth below.

4,4,7,7, 10beta-Pentamethyl-trans-decal-3beta-ol (PCR II-23) (2). A solution of 0.16g (0.72 mmol) of 1 in 6 mL of acetic acid, to which was added 100 mg of platinum (IV) oxide, was hydrogenated at 30 psi in a Paar 3991 apparatus heated to 500° C. by external heating tape regulated by an Omega 920 temperature controller for 24 hours. The mixture was then diluted with 20 mL of ethyl acetate, filtered and evaporated. The residue was dissolved in 30 mL of ether, washed with saturated aqueous sodium carbonate, water and saturated aqueous sodium chloride. The ethereal layer was dried over anhydrous sodium sulfate and evaporated to afford 0.22g of residue which was flash chromatographed to yield 0.15g (94%) of 2, mp 105°–1060° C. after recrystallization from hexane-ethyl acetate; IR 3280, 2920 cm$^{-1}$; $^1$H NMR delta 3.23 (dd, J=7.5, 8.4 Hz, 1H), 1.65–1.05 (m, 12H), 0.95 (s, 3H) 0.93 (s, 3H), 0.88 (s, 3H), 0.87 (s, 3H), 0.74 (s, 3H), $^{13}$C NMR delta 79.38, 47.35, 41.15, 39.92, 38.39, 34.97, 34.48, 34.02, 33.61, 30.90, 27.62, 25.35, 18.62, 14.90; MS m/e 224 (M+, 17.31), 191 (57.91), 167 (37.83), 166 (31.19), 165 (48.97), 137 (29.06), 123 (20.84), 111 (100), 109 (63.14) Anal. calcd for C15H280; C, 80.29; H, 12.58. Found: C, 80.36; H, 12.53.

Inhibition of sterol synthesis by PCR II-23 was determined as set forth in Example 1.

Cytotoxicity was determined by measuring the effects of the inhibitor on hepatocyte protein synthesis. Primary rat hepatocytes (2.2×10$^6$ cells/60 mm dish) were preincubated overnight with various concentrations of inhibitor. The media containing the inhibitor was removed and replaced with fresh media containing the same concentration of inhibitor and [$^{35}$S]-methionine, and incubated for 1 hour. The cells were harvested, taken to 5% trichloroacetic acid to precipitate protein, filtered on a fiberglass filter and counted for incorporation of [$^{35}$]-methiononine into protein. Cytotoxicity was measured relative to control hepatocyte cultures without inhibitor.

Example 5 (JW I-60 Synthesis)

4,4,10beta-trimethyl-9beta-hydroxymethyl-trans-decal-3beta-ol (JW I-60) is an weak inhibitor of cholesterol synthesis but a much more effective inhibitor of fatty acid synthesis. Hypertriglyceridemia and hypercholesterolemia both promote the development of atherosclerosis.

The syntheis of JW I-60 was somewhat analogous to that of PCR II-8B. The starting ketoalcohol is known. See Westerkaemper, John "An Attempted Synthesis of beta-Azidomethyl-6 beta-hydroxy-5, 5, 8 alpha-trimethyl-1, 2,3,4,4a,5,6,7,8,8a-decahydronaphthalene: A Prospective Photosaffinity Label for Oxidosqualene Cyclase," Honors Thesis, Dartmouth College (1986); Reuvers and DeGroot; J. Org. Chem., 49: 110–13 (1984). However, the methylidine alcohol was converted into JW I-60 by oxidative hydroboration —See Brown, *Organic Synthesis Via Boranes*, 55 (John Wiley & Sons: 1975).

A more detailed description of the synthesis follows.

4,4,10beta-Trimethyl-9-methylidene-trans-decal-3beta-ol (8). Into a 250-mL three-necked flask was placed 0.788g of 60% NaH (19.7 mmol), which was washed three times with hexane and dried with a stream of nitrogen. Dry THF (80 mL) was a d d e d f o l l ° w ed b y 8 . 1 3 g ( 2 0 . 1 m m o l) of methyltriphenylphosphonium iodide. The resulting mixture was stirred overnight and then the yellow solution was heated at 50° C for 90 minutes. The ylide solution was transferred under nitrogen via a cannula into another dry flask, care being taken not to transfer the NaI precipitate. The THF was removed first by distillation at atmospheric pressure followed by vacuum distillation at room termperature. The ylide was dried for 90 minutes at 0.5 torr and then dissolved in 60 mL of benzene with warming to facilitate the solvation. A solution of 0.206g (0.98 mmol) of 7, prepared as previously described, in 8 mL of benzene was placed in a 100-mL three necked flask fitted with a nitrogen inlet and a pressure equalizing dropping funnel and was heated to 70° C. A 15-mL portion of the ylide solution was added dropwise over 1 hour. TLC indicated that a little starting material remained so an additional 15 mL of the ylide solution was added over 15 minutes. The mixture was stirred for another 15 minutes, cooled to room temperature, and excess ylide was decomposed by the addition of 5 mL of acetone. The solvents were removed under reduced pressure and chromatography of the residue using hexane-ethyl acetate gave 0.146g (72%) of 8, mp 96°–98° C. Two recrystallizations from hexane and sublimation at 0.35 torr and 57° C yielded 8, mp 99.8100.0° C; IR 3350, 1635, 890 cm$^{-1}$; $^1$H NMR delta 4.5 (s, 2H), 3.2 (m, 1H), 2.25 (sextet, 1H), 2.1 (m, 1H), 1.1–2.0 (m, 10H), 1.05 (s, 3H), 0.95 (s, 3H), 0.8 (s, 3H); $^{13}$C NMR delta 159.69, 102.76, 78.91, 53.09, 39.72, 39.39, 35.29, 32.93, 28.59, 28.11, 27.72, 21.86, 20.72, 15.42 Anal. Calcd for C$_{14}$H$_{24}$O; C, 80.71; H, 11.61. Found: C, 80.41; H, 11.71.

4,4,10beta-Trimethyl-9beta-hydroxymethyl-trans-decal-3beta-ol (JW I-60) (3). Freshly distilled THF (2 mL) was placed into a 50-mL round-bottomed flask containing 0.765g (3.67 mmol) of 8. The system was flushed with nitrogen and 22 mL (11 mmol) of a 0.5M solution of 9-BBN in THF was added dropwise over 1 hour. Evolution of gas was observed during the addition of the first 10 mL of solution. The solution was stirred for 3 hours, after which time 3 mL of 3 M NaOH solution was added slowly with evolution of gas. The solution was cooled to 0° C., and then 3 mL of 30% hydrogen peroxide was added dropwise. The solution was stirred for 30 minutes, after which time potassium carbonate was added to saturate the aqueous phase. The aqueous layer was removed and washed with 3×10 mL of ether. The organic layers were combined, washed with 25 mL of brine dried over magnesium sulfate, and evaporated toyyield an oily residue which was chromatographed using hexane-ethyl acetate to afford 0.699g (84%) of material, mp 141°–148° C., which $^{13}$C NMR showed to be predominantly 3 contaminated with an unidentified substance. Five recrystallizations from hexane-ethyl acetate afforded pure 3, mp 161–162, IR-3320 cm$^{-1}$: $^1$H NMR delta 3.83 (d, J=3Hz, 1H), 3.80 (d, J=3Hz, 1H), 3.26 (m, 3H), 1.90–1.10 (m, 12H), 0.98 (s, 3H), 0.83 (s, 3H), 0.83 (s, 3H), 0.79 (s, 3H); $^{13}$C NMR delta 78.83, 63.56, 54.26, 53.67, 38.97, 37.43, 36.61, 28.25, 27.40, 26.88, 25.31, 21.61, 15.52, 14.51; MS, m/e 226 (M+, 1.410, 208 (43.47), 193 (13.06), 175 (15.50), 121 (100). Anal. Calcd for C$_{14}$H$_{26}$O$_2$; C, 74.29; H, 11.58. Found: C, 74.14; H, 11.63.

Reference Example 1

Melting points were determined by using a Thomas-Hoover melting point apparatus and are uncorrected. Infrared (IR) spectra were recorded on a Perkin-Elmer 599 spectrometer and referenced to the 1601 cm$^{-1}$ band of polystyrene. Samples were analyzed as thin films on NaCl plates. The 1H Nuclear Magnetic Resonance (N were recorded on Varian EM 360A (60 MHz) and Varian XL-300 (300 MHz) instruments using CDCL$_3$ as solvent. $^{13}$C NMR spectra were determined on a Varian XL-300 spectrometer using CDCL$_3$ a solvent. Both $^1$H and $^{13}$C NMR spectral data are presented in parts per million (delta) downfield relative to tetramethylsilane as internal standard. The $^1$H NMR data are tabulated in order; multiplicity, coupling constant and number of protons. Mass spectral (MS) analyses were performed on a Finnnigan 4023 Gas chromatography/Mass spectrometer at 70 eV (direct insertion) and the MS data are presented as m/e (intensity expressed as percent of base peak). Elemental analyses were carried out by Atlantic Microlab Inc., Atlanta, GA.

Analytical thin layer chromatography (TLC) was performed on EM Silica gel 60 G254 plates (0.2 mm) and visualized under ultraviolet light or with p-anisaldehyde-H2S04-EtOH spray. Flash chromatography was carried out with EM Reagent silica gel 60 (230-400 Mesh) using hexane-ethyl acetate mixtures.

Ether was distilled from lithium aluminum hydride and benzene from sodium, under an atmosphere of nitrogen. Tetrahydrofuran (THF) was distilled from potassium using benzophenone as an indicator. Methyltriphenylphosphonium bromide, methyltriphenylphosphonium iodide, 9-borabicyclo [3.3.1]nonane (BBN, 05 M in tetrahydrofuran), sodium tpentoxide, silver acetate, silver wool (gold label), granular zinc (10 mesh), crystalline platinum (IV) oxide, diethyl zinc (1.1 M in toluene) and diiodomethane were purchased from Aldrich.

Example 6: Effect on HepG2 LDL Receptor

We have compared LA-I-140 and LN-I-83 with the conventional squalene oxide cyclase inhibitors U186-66A and TMD by studying their effect on the LDL receptor of HepG2 cells.

The assay is essentially as described by Goldstein, Basu and Brown (Methods in Enzymology, 98: 241-260, 1983). Briefly, confluent cultures of HepG2 cells are incubated for 24 hours in cholesterol-free medium to induce LDL receptors. Test compounds are added to the medium at appropriate concenrations during this incubation. At the end of 24 hours [$^{125}$I]labeled LDL (200-400 cpm/ng) is added to the medium (10-50 ug LDL protein/ml) and the cells are incubated at 37° C. for 3-6 hours.

(a) Degradation of $^{125}$I-LDL: The culture medium is removed from the monolayer of cells and undegraded LDL is precipitated with 10% (w/v) trichloroacetic acid.

The supernatant fraction is treated with 5% (w/v) silver nitrate to precipitate any free iodine. The radioactivity in the final supernatant fraction, which represents monoiodotyrosine, the proteolytic degradation product of $^{125}$I-LDL, is measured in a gamma counter.

(b) Specific binding of $^{125}$I-LDL: The cell monolayers are washed in a cold room (4° C.) three times rapidly with ice-cold buffer B (150 mM NaCl, 50 mM TrisHCl, pH 7.4 and 2 mg/ml bovine serum albumin). Each monolayer is incubated in buffer B for 10 minutes followed by one wash with buffer C (buffer B with bovine serum albumin omitted). Receptor-bound LDL is then released form cell surface by adding buffer D (50 mM NaCl, 10 mM HEPES, pH 7.4, 4 mg/ml dextran sulfate) and incubating at 4° C for 60 minutes on a rotary shaker (60 rotations per minute). An aliquot of buffer D is counted to determine the amount of $^{125}$I-LDL released from cell surface.

Internalization of $^{125}$I-LDL: After removal of buffer D, the cell monolayers are dissolved in 0.1 N NaOH by incubation overnight at 37° C. in a humidified incubator. The alkaline digest is briefly homogenized with the aid of a sonicator and aliquots are withdrawn for the determination of internalized radioactivity and for measurement of cell protein. All values are normalized for 1 mg of cell protein. The results are shown n Table 1 below:

TABLE 1

$^{125}$I-LDL Metabolism in the HepG2 Cells Treated with Various Inhibitors of Squalene Oxide Cyclase (ng/mg cell protein)

| Treatment | Binding | Internal | Degradation |
|---|---|---|---|
| None | 57 ± 3 | 374 ± 9 | 701 ± 38 |
| U18666A (5 ug/ml) | 160 ± 4 | 1093 ± 17 | 682 ± 141 |
| TMD (20 ug/ml) | 130 ± 11 | 891 ± 202 | 990 ± 71 |
| LA-I-140 (20 ug/ml) | 75 ± 3 | 642 ± 96 | 408 ± 61 |
| LN-I-83 (20 ug/ml) | 105 ± 12 | 687 ± 152 | 864 ± 47 |

In the case of PCR-II-23 and PCR-II-8B, we have examined their binding to the LDL receptors both when administered alone and in the presence of "down" regulators of this receptor (Table 2).

We find (Table 2) that both mevinolin and PCR compounds are equally effective in up regulation of LDL receptors in HepG2 cells in culture medium free of sterol supplements (HDF-high density fraction of serum). However, as expected, although mevalonate effectively suppresses the mevinolin stimulation of LDL receptors, it has no effect on the up regulation of receptors by the squalene oxide cyclase inhibitors. These results, taken together, confirm the rationale that late blocks in the cholesterol synthesis, like the early blocks produced by mevinolin can effectively up regulate LDL receptors and that this up regulation is a consequence of the inhibition of cholesterol synthesis by these compounds.

TABLE 2

Effect of down regulators of the LDL receptor on receptor induction by inhibitors of endogenous sterol synthesis.

| Suppressor | LDL BINDING (ng/mg cell protein ± SEM) | | | |
|---|---|---|---|---|
| | HDF | PCR-II-23 | PCR-II-8B | Mevinolin |
| None | 88 ± 6 | 281 ± 18 | 278 ± 3 | 213 ± 4 |
| LDL (200 ug/ml) | 27 ± 2 | 36 ± 2 | 39 ± 4 | 38 ± 3 |
| 25-hydroxy-cholesterol (5 ug/ml) | 34 ± 3 | 117 ± 11 | 69 ± 4 | 3 ± 2 |
| Mevalonate (10 mM) | 19 ± 2 | 196 ± 30 | 176 ± 17 | 35 ± 2 |

Example 7: Effect on Rat Liver Microsomal SOC Activity

Using a rat liver microsomal squalene oxide cyclase assay, we have determined the dose at which these drugs and TMD reduce squalene oxide cyclase activity to one-half its normal value.

Rat liver microsomes (S$_{105}$-rat liver homogenate) were prepared by the method of Popjak, G (Methods in Enzymology, 1969 XV, 393-545). The reaction mixture contained [$^3$H]-(S)-22,3-oxidosqualene (40 uM final), Tween-80 (0.15% w/v final), 0.1 M potassium phosphate, pH 7.5, and inhibitor of varying concentration all in 0.8 ml. The reaction was initiated by the addition of 0.2 ml of the SIO homogenate. The reaction was flushed with N$_2$ and incubated anaerobically for 1 hour at 37° C. The reaction was terminated by addition of 1 ml of 6% potassium hydroxide in methanol (w/v). The mixture was left overnight in the cold and the sterols were then extracted 3 times with hexane, combined, and dried over anhydrous sodium sulfate. After reduction to ryness, cold lanosterol was added as carrier, and the extract was applied to a silica TLC plate. After development in methylene chloride, the spot corresponding to lanosterol was scraped off and counted for radioactivity. The I50 for each inhibitor was determined from a plot of radioactive lanosterol formed versus inhibitor concentration.

Based on this assay, we obtained the following values for the dosage (I50) needed to suppress half the SOC activity:

TABLE 3

| Compound | $I_{50}$ |
|---|---|
| TMD | 430 uM |
| LN I-83 | 430 uM |
| PCR II-23 | 160 uM |
| PCR II-8B | 80 uM |

Thus, PCR II-23 and PCR II-8B are about 2.7 and 5.4 times, respectively, as effective as TMD as SOC inhibitors.

References and Notes

1 Nelson, J. A.; Czarny, M. R.; Spencer, T. A. *Bioorganic Chem.* 1982,11, 371–381. See also: Mukherjee, S. L.; Dutta, P.C. *J. Chem. Soc.* 1960, 67–71.
2. Middleton, W. J. *J. Org. Chem.* 1975, 40, 574–578.
3. Czarny, M. R., Ph.D. Dissertation, Dartmouth College, 1976; Gaspert, B.; Halsall, T. G.; Willis, D. *J. Chem. Soc.* 1958, 624–628.
4. Meinwald, J.; Tufariello, J. J.; Hurst, J. J. *J. Org. Chem.* 1964, 29, 2914–2919.
5. Shioiri, T.; Ninomiya, K.: Yamada, S. *J. Am. Chem. Soc.* 1972, 94, 6203–6205, Capson, T. L.: Poulter, C. D. *Tetrahedron Lett.* 1984, 3515–3518.
6. Harding, K. E.; Burks, S. R. *J. Org. Chem.* 1981, 46, 3920–3922; Harding, K. E.; Marman, T.H. *J. Org. Chem.* 1984, 49, 2838–2840.
Still, W. C.; Kahn, M.; Mitra, A. *J. Org. Chem.* 1978, 43, 23–2925.
8. Ohtsuka, M.; Yoshinori, F.; Nobuo, I. *Chem. Pharm. Bull.* 1986, 34, 2780–2785.
9. Nelson, J. A.; Czarny, M. R.; Spencer, T. A.; Limanek, J. S.; McCrae, K. R.; Chang, T. Y. *J. Am. Chem Soc.* 1978, 100, 4900–4902.
10. Bowers, A.; Halsall, T. G.; Jones, E. R. H.; Lemin, A *J. Chem. Soc.* 1953, 2548–2560.

We claim:

1. A compound having one of the structure shown in formulas (I) and (II) below:

(I)

(II)

wherein
$R_1$ is methyl, ethyl, or forms a cyclopropane ring with $R_2$;
$R_2$ is methyl, ethyl, or forms a cyclopropane ring with $R_1$, but $R_1$ and $R_2$ are not both ethyl;
$R_3$ is hydrogen, an alkyl of no more than five carbon atoms, fluorine, chlorine or bromine;
$R_4$ is hydrogen, an hydroxy alkyl of no more than 5 carbon atoms, fluorine, chlorine or bromine, where $R_3$ and $R_4$ may be the same or different, and where $R_3$ and $R_4$ may form a cyclopropane ring;
$R_5$ is hydrogen, methyl, ethyl, propyl, isopropyl, or $CH_2OH$;
$R_6$ is hydrogen, methyl or ethyl; and
$R_7$ is hydrogen, methyl or ethyl;
and wherein if the compound is of formula (I), then one or more of $R_3$, $R_4$ or $R_5$ is not hydrogen.

2. A compound according to claim 1 wherein the compound is of formula (I) and $R_3$ or $R_4$ is not hydrogen.

3. A compound according to claim 2 wherein $R_1$, $R_2$ and $R_6$ are methyl, $R_3$ and $R_4$ are fluorine, and $R_5$ is hydrogen.

4. A compound according to claim 2 wherein $R_1$, $R_2$, $R_3$, $R_4$ and $R_6$ are methyl and $R_5$ is hydrogen.

5. A compound according to claim 1 wherein the compound is of formula (I) and $R_5$ is not hydrogen.

6. A compound according to claim 5 wherein $R_1$, $R_2$ and $R_6$ are methyl, $R_3$ and $R_4$ are hydrogen, and $R_5$ is $-CH_2OH$.

7. A method of inhibiting the activity of squalene oxide cyclase which comprises admixing the compound of claim 1 in an enzyme inhibitor amount with material known to contain squalene oxide cyclase.

8. A compound according to claim 1 wherein the compound is of formula (II).

9. The compound of claim 8 wherein $R_1$, $R_2$ and $R_6$ are methyl and $R_3$, $R_4$, $R_5$ and $R_7$ are hydrogen.

10. A pharmaceutical composition comprising a therapeutically effective amount of the compound of claim 1 and a pharmaceutically acceptable carrier.

11. A method of regulating cholesterol levels in a mammal which comprises administering to the mammal an effective amount a compound according to claim 1 which is an inhibitor of squalene oxide cyclase at a dosage nontoxic to said mammal.

12. The compound of claim 1, wherein the compound is further selected from the group consisting of compounds having a squalene oxide cyclase inhibitory activity in rat heptocytes exceeding that of TMD.

* * * * *